(12) United States Patent
Stites

(10) Patent No.: US 8,344,184 B2
(45) Date of Patent: Jan. 1, 2013

(54) METHODS FOR PROMOTING SYNGAS-TO-ALCOHOL CATALYSIS

(75) Inventor: Ronald C. Stites, Brighton, CO (US)

(73) Assignee: Albemarle Corporation, Baton Rouge, LA (US)

( * ) Notice: Subject to any disclaimer, the term of this patent is extended or adjusted under 35 U.S.C. 154(b) by 436 days.

(21) Appl. No.: 12/633,982

(22) Filed: Dec. 9, 2009

(65) Prior Publication Data

US 2010/0152497 A1    Jun. 17, 2010

Related U.S. Application Data

(60) Provisional application No. 61/122,212, filed on Dec. 12, 2008.

(51) Int. Cl.
*C07C 31/02* (2006.01)
*B01J 23/04* (2006.01)
*B01J 27/051* (2006.01)

(52) U.S. Cl. .................. 568/840; 502/220; 502/344

(58) Field of Classification Search ............... 568/840; 502/220, 344
See application file for complete search history.

(56) References Cited

U.S. PATENT DOCUMENTS

| | | | |
|---|---|---|---|
| 4,752,623 | A | 6/1988 | Stevens |
| 4,935,395 | A | 6/1990 | Mahajan et al. |
| 5,385,949 | A | 1/1995 | Tierney et al. |
| 6,028,119 | A | 2/2000 | Kokubu et al. |
| 6,921,733 | B2 | 7/2005 | Mahajan |
| 7,196,239 | B2 | 3/2007 | Van Egmond et al. |

*Primary Examiner* — Sikarl Witherspoon
(74) *Attorney, Agent, or Firm* — Jeremy J. Kliebert; Marcy M. Hoefling; James A. Jubinsky

(57) ABSTRACT

Improved methods of introducing promoters to catalysts are described. The present invention provides a convenient method of uniformly distributing a catalyst promoter, to provide for intimate contact between the promoter and the active catalyst sites. This intimate contact can enhance the activity and/or product selectivity of the promoted catalyst. In some embodiments, the method includes reacting an alkali metal with an alcohol in a non-aqueous medium, contacting the resulting solution with a starting catalyst, and depositing the alkali metal onto the starting catalyst to form an alkali-promoted catalyst.

31 Claims, No Drawings

METHODS FOR PROMOTING SYNGAS-TO-ALCOHOL CATALYSIS

PRIORITY DATA

This patent application claims priority under 35 U.S.C. §120 from U.S. Provisional Patent Application No. 61/122,212 for "METHODS FOR PROMOTING SYNGAS-TO-ALCOHOL CATALYSIS," filed Dec. 12, 2008, the disclosure of which is hereby incorporated by reference herein for all purposes.

FIELD OF THE INVENTION

The present invention generally relates to the field of heterogeneous catalysts, and more specifically to methods of adding promoters to these catalysts.

BACKGROUND OF THE INVENTION

One of the steps commonly required for the synthesis of a heterogeneous catalyst involves the deposition of a component generically known as a "promoter," which might be an anionic, cationic, or molecular species, onto a surface of a catalytic material. The deposition process is usually intended to disperse the promoter broadly and uniformly.

The promoter is sometimes deposited out of the gas phase, as for example when HCl carried by an inert gas is reacted with a metal oxide, or when a metal is introduced by vaporizing its volatile carbonyl compounds into a carrier gas and decomposing the metal carbonyl onto the surface of a catalyst precursor.

In some situations a promoter that is ionic is deposited onto a catalyst precursor from solution in a polar solvent by ion exchange. This process requires that the catalyst precursor carry ionic groups on its surface so that a species that is usually a surface cation can be exchanged by a different cation out of a concentrated solution. This process is employed, for example, when a zeolite bearing oxide anions bound to the zeolite framework and neutralized by sodium countercations, is converted to the acid form with proton countercations by exchange with aqueous ammonium cations followed by calcination to drive off ammonia.

Adsorption is a related process wherein a catalyst precursor extracts the promoter out of solution. Van der Waals forces can attach the promoter to the catalyst precursor (no exchangeable ions are involved).

A catalyst promoter is sometimes added by dry-mixing the promoter and catalyst precursor solids and allowing the promoter to migrate to the catalyst surface as it is melted, volatilized, or otherwise rendered mobile inside the catalytic reactor in the presence of heat, reactants, and products.

Another method for introducing a promoter onto a catalyst precursor involves dissolving a promoter in water, and then depositing the promoter by evaporating the water. If the volume of solvent involved is about equal to the catalyst precursor pore volume, then the procedure is called "incipient wetness impregnation." Alternately, the catalyst precursor can be stirred with an excess volume of solution and the slurry evaporated to dryness so that the promoter originally in solution is deposited onto the catalyst surface. If enough solvent is used to cause the catalyst precursor to be conspicuously wetted, then the procedure is known as "solvent impregnation."

Each of these procedures has limitations. Promoter deposition from the gas phase requires that the promoter have a volatile form. The ion-exchange method requires both the catalyst precursor and the promoter be ionic, and further that the ion-exchange sites be the desired destination for the promoter. Adsorption forces may not be sufficiently strong. The deposition of a promoter from excess water (or other solvent) by impregnation can lead to surface chemistry that may not be beneficial.

In view of these limitations, improved methods of introducing promoters to catalysts are needed. Specifically, there is a need for practical methods to disperse promoters onto the surface of catalysts or catalyst precursors, wherein the dispersion leads to a substantially uniform promoter composition and efficient use of the promoter.

What is especially needed is a convenient method of uniformly distributing a catalyst promoter, to provide for intimate contact between the promoter and the active catalyst sites, wherein such intimate contact enhances the activity and/or product selectivity of the promoted catalyst.

SUMMARY OF THE INVENTION

In some variations, this invention provides a method of generating an alkali-promoted catalyst, the method comprising:

(a) providing an alkali metal in a non-aqueous medium;
(b) providing an alcohol;
(c) reacting, at least in part, the alkali metal with an excess of the alcohol, thereby producing a promoter solution comprising the alcohol and the alkoxide of the alkali metal;
(d) providing a starting catalyst; and
(e) contacting at least some of the promoter solution from step (c) with the starting catalyst, under effective conditions to deposit at least some of the alkali metal onto the starting catalyst, thereby producing an alkali-promoted catalyst.

In some embodiments, the alkali metal is selected from the Group IA elements, such as K and/or Cs. The alcohol can be selected from $C_1$-$C_8$ linear or branched alcohols. For example, methanol can be employed. In some embodiments, the non-aqueous medium comprises the alcohol. In other embodiments, the non-aqueous medium does not include the alcohol.

In some embodiments, the method includes adjusting the concentration of the alkali metal in the non-aqueous medium to control the amount of the alkali metal deposited in step (e). In some embodiments, the method includes adjusting the alkali-metal concentration to control the distribution of the alkali metal deposited in step (e).

Step (e), in some embodiments, comprises generating an immobile salt of the alkali metal. In some embodiments, step (e) comprises reaction of the alkali alkoxide with an acidic species at the surface of the starting catalyst.

In certain embodiments, step (d) further comprises treating the starting catalyst to generate a plurality of hydrogen acid sites.

Optionally, step (e) can include treating the starting catalyst or the alkali-promoted catalyst with a gas containing hydrogen, such as $H_2$ or $H_2S$.

The alkali-promoted catalyst can be combined with a binder material and/or added to a support phase, in various embodiments.

In some embodiments, the concentration of the alkali metal in the non-aqueous medium is adjusted to control the depth, into the support phase, of the alkali metal deposited in step (e).

An exemplary starting catalyst comprises Mo, Co, and S. An exemplary alkali-promoted catalyst comprises Mo, Co, S, and K. Another exemplary alkali-promoted catalyst comprises Mo, Co, S, and Cs.

In preferred embodiments, the selectivity of syngas conversion toward alcohols is higher for the alkali-promoted catalyst than for the starting catalyst. The method of the invention can be extended to include use of the alkali-promoted catalyst for generation of one or more $C_1$-$C_4$ alcohols from syngas.

In certain embodiments, the invention provides a method of generated an alkali-promoted Mo—Co—S catalyst, the method comprising:

(a) providing an alkali metal in a non-aqueous medium, wherein the alkali metal is K or Cs;

(b) providing an alcohol soluble in the non-aqueous medium;

(c) reacting, at least in part, the alkali metal with an excess of the alcohol, thereby producing a promoter solution comprising the alcohol and the alkoxide of the alkali metal;

(d) providing a starting Mo—Co—S catalyst; and (e) contacting at least some of the promoter solution from step (c) with the starting catalyst, under effective conditions to deposit at least some of the alkali metal onto the starting catalyst, thereby producing an alkali-promoted Mo—Co—S catalyst.

Another variation of the invention relates to catalyst compositions produced in accordance with the methods described herein. For example, in some embodiments, a catalyst composition is produced by a process comprising the steps of:

(a) providing an alkali metal in a non-aqueous medium, wherein the alkali metal is K or Cs;

(b) providing an alcohol soluble in the non-aqueous medium;

(c) reacting, at least in part, the alkali metal with an excess of the alcohol, thereby producing a promoter solution comprising the alcohol and the alkoxide of the alkali metal;

(d) providing a starting Mo—Co—S catalyst; and (e) contacting at least some of the promoter solution from step (c) with the starting catalyst, under effective conditions to deposit at least some of the alkali metal onto the starting catalyst, thereby producing an alkali-promoted Mo—Co—S catalyst.

Other variations of the invention provide a method of generating an alkali-promoted catalyst employing the following steps:

(a) providing an alkoxide comprising a selected alkali metal;

(b) providing an alcohol;

(c) dissolving the alkoxide into the alcohol, thereby producing a promoter solution comprising the alkoxide and alcohol;

(d) providing a starting catalyst; and (e) contacting at least some of the promoter solution from step (c) with the starting catalyst, under effective conditions to deposit at least some of the selected alkali metal onto the starting catalyst, thereby producing an alkali-promoted catalyst.

In certain embodiments, an alkali-promoted Mo—Co—S catalyst is generated according to the following method steps:

(a) providing an alkoxide comprising K or Cs;

(b) providing a $C_1$-$C_8$ alcohol;

(c) dissolving said alkoxide into said alcohol, thereby producing a promoter solution comprising said alkoxide and said alcohol;

(d) providing a starting Mo—Co—S catalyst; and (e) contacting at least some of said promoter solution from step (c) with said starting catalyst, under effective conditions to deposit at least some of said selected alkali metal onto said starting catalyst, thereby producing an alkali-promoted Mo—Co—S catalyst.

Catalyst compositions can be produced by a process comprising the steps of:

(a) providing an alkoxide comprising K or Cs;

(b) providing a $C_1$-$C_8$ alcohol;

(c) dissolving said alkoxide into said alcohol, thereby producing a promoter solution comprising said alkoxide and said alcohol;

(d) providing a starting Mo—Co—S catalyst; and (e) contacting at least some of said promoter solution from step (c) with said starting catalyst, under effective conditions to deposit at least some of said selected alkali metal onto said starting catalyst, thereby producing an alkali-promoted Mo—Co—S catalyst.

The invention also includes apparatus for carrying out the disclosed methods.

DETAILED DESCRIPTION OF EMBODIMENTS OF THE INVENTION

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used herein, "$C_1$-$C_4$ alcohols" means one or more alcohols selected from methanol, ethanol, propanol, and butanol, including all known isomers of such compounds.

The present invention will now be described by reference to the following detailed description which characterizes and illustrates some preferred embodiments for producing ethanol. This description by no means limits the scope and spirit of the present invention.

In some variations, this invention provides a method of generating an alkali-promoted catalyst, the method comprising:

(a) providing an alkali metal in a non-aqueous medium;

(b) providing an alcohol;

(c) reacting, at least in part, the alkali metal with an excess of the alcohol, thereby producing a promoter solution comprising the alcohol and the alkoxide of the alkali metal;

(d) providing a starting catalyst; and (e) contacting at least some of the promoter solution from step (c) with the starting catalyst, under effective conditions to deposit at least some of the alkali metal onto the starting catalyst, thereby producing an alkali-promoted catalyst.

In some embodiments, the alkali metal is selected from the Group IA elements, such as K and/or Cs. The alcohol can be selected from $C_1$-$C_8$ linear or branched alcohols. For example, methanol can be employed. In some embodiments, the non-aqueous medium comprises the alcohol. In other embodiments, the non-aqueous medium does not include the alcohol.

In some embodiments, the method includes adjusting the concentration of the alkali metal in the non-aqueous medium to control the amount of the alkali metal deposited in step (e). In some embodiments, the method includes adjusting the alkali-metal concentration to control the distribution of the alkali metal deposited in step (e). In some embodiments, the concentration of the alkali metal in the non-aqueous medium is adjusted to control the depth, into the support phase, of the alkali metal deposited in step (e).

Step (e), in some embodiments, comprises generating an immobile salt of the alkali metal. In some embodiments, step (e) comprises reaction of the alkali alkoxide with an acidic species at the surface of the starting catalyst. In certain embodiments, step (d) further comprises treating the starting catalyst to generate a plurality of hydrogen acid sites. Optionally, step (e) can include treating the starting catalyst or the alkali-promoted catalyst with a gas containing hydrogen, such as $H_2$ or $H_2S$.

Other variations of the invention are premised on the realization that rather than generating an alkoxide in solution, it is possible to dissolve an alkoxide into a suitable alcohol. Preferably, the alkoxide (or plurality of alkoxides) is selected for the desired alkali metal(s). The alcohol can be selected based on viscosity and boiling point, solubility for the selected alkoxide(s), or other properties. For example, when potassium is the desired alkali metal, potassium methoxide ($KOCH_3$) can be dissolved into methanol and the $KOCH_3$/$CH_3OH$ solution then contacted with the starting catalyst, under effective conditions to deposit at least some of the potassium onto the starting catalyst, thereby producing an potassium-promoted catalyst.

An exemplary starting catalyst comprises Mo, Co, and S. An exemplary alkali-promoted catalyst comprises Mo, Co, S, and K. Another exemplary alkali-promoted catalyst comprises Mo, Co, S, and Cs. The alkali-promoted catalyst can be combined with a binder material and/or added to a support phase.

In some embodiments, various metal dopants can be introduced by first dissolving the corresponding metal oxides into the alcohol, followed by contacting at least some of the solution with an undoped catalyst, under effective conditions to deposit at least some of the metal dopant(s) onto the catalyst, thereby producing a doped catalyst. Exemplary metal dopants include Co, Re, and Rh.

$MoS_2$ can be an effective catalyst for synthesis of alcohols, such as methanol or ethanol, when it is promoted by certain compounds of alkali metals. In various embodiments of the invention, a base promoter may be present in free or combined form. The base promoter can be present as a metal, oxide, carbonate, hydroxide, sulfide, as a salt, in a compound with another component, or some combination of these. Typically, for reasons of convenience and/or cost, base promoters are in compound form rather than pure elements.

In some embodiments, at least one base promoter includes potassium or cesium. In some embodiments, at least one base promoter includes one or more elements selected from the group consisting of barium, strontium, scandium, yttrium, lanthanum, or cerium, in free or combined form. Due to the higher valence of these base promoters, the elemental forms of these metals—or their corresponding salts, oxides, or sulfides—will typically not very volatile. Lower volatility can be preferred. The base promoter is generally initially present in an amount of at least 0.1-20 wt % in the catalyst composition. Preferably, the base promoter is initially present in an amount of at least 5 wt %.

Another aspect of the invention provides for use of catalyst materials produced, in a reactor for synthesis of alcohols, preferably $C_1$-$C_4$ alcohols, such as ethanol.

The reactor is any apparatus capable of being effective for producing at least one $C_1$-$C_4$ alcohol from the syngas stream fed. The reactor can be a single vessel or a plurality of vessels. The reactor contains at least one catalyst composition that tends to catalyze the conversion of syngas into alcohols. The "reactor" can actually be a series or network of several reactors in various arrangements. For example, in some variations, the reactor comprises a large number of tubes filled with one or more catalysts as provided herein.

The reactor for converting syngas into alcohols can be engineered and operated in a wide variety of ways. The reactor operation can be continuous, semicontinuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal. A vertical configuration can be preferable.

In some embodiments, fresh syngas is produced according to methods described in Klepper et al., "Methods and apparatus for producing syngas," U.S. patent application Ser. No. 12/166,167 (filed Jul. 1, 2008), the assignee of which is the same as the assignee of the present application. U.S. patent application Ser. No. 12/166,167 is hereby incorporated by reference herein in its entirety.

Any suitable catalyst or combination of catalysts may be used in a reactor to catalyze reactions converting syngas to alcohols. Suitable catalysts may include, but are not limited to, those disclosed in U.S. patent application Ser. No. 12/166,167. Preferred catalysts minimize the formation of $CO_2$ and $CH_4$ under reaction conditions. Certain catalysts that can be used include Co—Mo—S materials promoted with potassium, which can be delivered (via precursor $K_2CO_3$) as described herein.

In some embodiments, conditions effective for producing alcohols from syngas include a feed hydrogen-carbon monoxide molar ratio ($H_2$/CO) from about 0.2-4.0, preferably about 0.5-2.0, and more preferably about 0.5-1.5. These ratios are indicative of certain embodiments and are not limiting. It is possible to operate at feed $H_2$/CO ratios less than 0.2 as well as greater than 4, including 5, 10, or even higher. It is well-known that high $H_2$/CO ratios can be obtained with extensive steam reforming and/or water-gas shift in operations prior to the syngas-to-alcohol reactor.

In some embodiments, conditions effective for producing alcohols from syngas include reactor temperatures from about 200-400° C., preferably about 250-350° C. Depending on the catalyst chosen, changes to reactor temperature can change conversions, selectivities, and catalyst stability. As is recognized in the art, increasing temperatures can sometimes be used to compensate for reduced catalyst activity over long operating times.

Preferably, the syngas entering the reactor is compressed. Conditions effective for producing alcohols from syngas include reactor pressures from about 20-500 atm, preferably about 50-200 atm or higher. Generally, productivity increases with increasing reactor pressure, and pressures outside of these ranges can be employed with varying effectiveness.

In some embodiments, conditions effective for producing alcohols from syngas include average reactor residence times from about 0.1-10 seconds, preferably about 0.5-2 seconds.

"Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In general, the specific selection of catalyst configuration (geometry), $H_2/CO$ ratio, temperature, pressure, and residence time (or feed rate) will be selected to provide, or will be subject to constraints relating to, an economically optimized process. The plurality of reactor variables and other system parameters can be optimized, in whole or in part, by a variety of means.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially. Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of generating an alkali-promoted catalyst, said method comprising:
   (a) providing an alkali metal in a non-aqueous medium;
   (b) providing an alcohol;
   (c) reacting, at least in part, said alkali metal with an excess of said alcohol, thereby producing a promoter solution comprising said alcohol and the alkoxide of said alkali metal;
   (d) providing a starting catalyst; and
   (e) contacting at least some of said promoter solution from step (c) with said starting catalyst, under effective conditions to deposit at least some of said alkali metal onto said starting catalyst, thereby producing an alkali-promoted catalyst.

2. The method of claim 1, wherein said alkali metal is selected from the Group IA elements.

3. The method of claim 2, wherein said alkali metal is K or Cs.

4. The method of claim 1, wherein said non-aqueous medium comprises said alcohol.

5. The method of claim 2, wherein said non-aqueous medium does not include said alcohol.

6. The method of claim 1, wherein said non-aqueous medium does not include said alcohol.

7. The method of claim 1, wherein said alcohol is selected from $C_1$-$C_8$ linear or branched alcohols.

8. The method of claim 7, wherein said alcohol is methanol.

9. The method of claim 1, further comprising adjusting the concentration of said alkali metal in said non-aqueous medium to control the amount of said alkali metal deposited in step (e).

10. The method of claim 1, further comprising adjusting the concentration of said alkali metal in said non-aqueous medium to control the distribution of said alkali metal deposited in step (e).

11. The method of claim 1, wherein step (e) comprises generating an immobile salt of said alkali metal.

12. The method of claim 1, wherein step (e) comprises reaction of said alkoxide with an acidic species at the surface of said starting catalyst.

13. The method of claim 1, wherein step (d) further comprises treating said starting catalyst to generate a plurality of hydrogen acid sites.

14. The method of claim 1, wherein step (e) further comprises treating said starting catalyst or said alkali-promoted catalyst with a gas containing $H_2$ and/or $H_2S$.

15. The method of claim 1, further comprising adding said alkali-promoted catalyst to a support phase.

16. The method of claim 15, wherein the concentration of said alkali metal in said non-aqueous medium is adjusted to control the depth, into said support phase, of said alkali metal deposited in step (e).

17. The method of claim 1, wherein said starting catalyst comprises Mo, Co, and S.

18. The method of claim 1, further comprising use of said alkali-promoted catalyst for generation of one or more $C_1$-$C_4$ alcohols from syngas.

19. A method of generating an alkali-promoted Mo—Co—S catalyst, said method comprising:
   (a) providing an alkali metal in a non-aqueous medium, wherein said alkali metal is K or Cs;
   (b) providing a $C_1$-$C_8$ alcohol soluble in said non-aqueous medium;
   (c) reacting, at least in part, said alkali metal with an excess of said alcohol, thereby producing a promoter solution comprising said alcohol and the alkoxide of said alkali metal;
   (d) providing a starting Mo—Co—S catalyst; and
   (e) contacting at least some of said promoter solution from step (c) with said starting catalyst, under effective conditions to deposit at least some of said alkali metal onto said starting catalyst, thereby producing an alkali-promoted Mo—Co—S catalyst.

20. A method of generating an alkali-promoted catalyst, said method comprising:
   (a) providing an alkoxide comprising a selected alkali metal;
   (b) providing an alcohol;

(c) dissolving said alkoxide into said alcohol, thereby producing a promoter solution comprising said alkoxide and said alcohol;

(d) providing a starting catalyst; and (e) contacting at least some of said promoter solution from step (c) with said starting catalyst, under effective conditions to deposit at least some of said selected alkali metal onto said starting catalyst, thereby producing an alkali-promoted catalyst.

21. The method of claim 20, wherein said alkali metal is selected from the Group IA elements.

22. The method of claim 21, wherein said alkali metal is K or Cs.

23. The method of claim 20, wherein said alcohol is selected from $C_1$-$C_8$ linear or branched alcohols.

24. The method of claim 23, wherein said alcohol is methanol.

25. The method of claim 20, wherein said alkoxide is potassium methoxide.

26. The method of claim 20, further comprising adjusting the concentration of said alkoxide in said alcohol to control the amount of said selected alkali metal deposited in step (e).

27. The method of claim 20, further comprising adjusting the concentration of said alkoxide in said alcohol to control the distribution of said selected alkali metal deposited in step (e).

28. The method of claim 20, wherein step (e) comprises generating an immobile salt of said selected alkali metal.

29. The method of claim 20, wherein step (e) comprises reaction of said alkoxide with an acidic species at the surface of said starting catalyst.

30. The method of claim 20, wherein said starting catalyst comprises Mo, Co, and S.

31. The method of claim 20, further comprising use of said alkali-promoted catalyst for generation of one or more $C_1$-$C_4$ alcohols from syngas.

* * * * *